(12) United States Patent
Wiegerinck et al.

(10) Patent No.: US 6,344,571 B2
(45) Date of Patent: Feb. 5, 2002

(54) WATER SOLUBLE ANALOGS AND PRODRUGS OF PACLITAXEL

(75) Inventors: Peter H. G. Wiegerinck, Arnhem; Duncan Sperling, Oss; Lesly Braamer, Zutphen; Eric W. P. Damen, Nijmegen; Johan W. Scheeren, Malden; Dick de Vos, Oegstgeest, all of (NL)

(73) Assignee: Pharmachemie B.V., Haarlem (NL)

( * ) Notice: Subject to any disclaimer, the term of this patent is extended or adjusted under 35 U.S.C. 154(b) by 0 days.

(21) Appl. No.: 09/788,344

(22) Filed: Feb. 21, 2001

Related U.S. Application Data

(63) Continuation of application No. PCT/NL98/00473, filed on Aug. 21, 1998.

(51) Int. Cl.$^7$ .................... C07D 305/14; A61K 31/337
(52) U.S. Cl. ................. 549/510; 549/511; 514/449
(58) Field of Search ................................. 549/510, 511

(56) References Cited

U.S. PATENT DOCUMENTS 5,059,699 A 10/1991 Kingston et al.

FOREIGN PATENT DOCUMENTS

WO 94/05282 3/1994

OTHER PUBLICATIONS

Damen et al, Bioorg. Med. Chem., 8(2), pp. 427–432, 2000.*

* cited by examiner

*Primary Examiner*—Ba K. Trinh
(74) *Attorney, Agent, or Firm*—Browdy and Neimark

(57) ABSTRACT

The invention relates to water soluble antitumor analogs of paclitaxel of formula (I) wherein $R_1$=C(O)CH$_2$CH(OH)COOX, $R_2$=H, C(O)CH$_2$CH(OH)COOX, X=H, Li, Na or any other pharmaceutically acceptable counterion, as well as to a pharmaceutical composition comprising an antineoplastically effective amount of such analogs as an active ingredient.

4 Claims, 3 Drawing Sheets

WATER SOLUBLE ANALOGS AND PRODRUGS OF PACLITAXEL

This application is a continuation of PCT/NL98/00473 dated Aug. 21, 1998.

FIELD OF INVENTION

The invention relates to water soluble prodrugs in which the solubulizing groups are non toxic acids which are attached to paclitaxel as an ester functionality to the C2'- and/or C7-hydroxyl position. These prodrugs are stable in aqueous solution but are readily hydrolyzed at physiological conditions to the parent drug.

BACKGROUND OF THE INVENTION

Paclitaxel (1) is a natural diterpenoid, isolated from the Pacific yew tree (*Taxus brevifolia*). Paclitaxel has been approved for treatment of patients with advanced ovarian cancer or breast cancer.

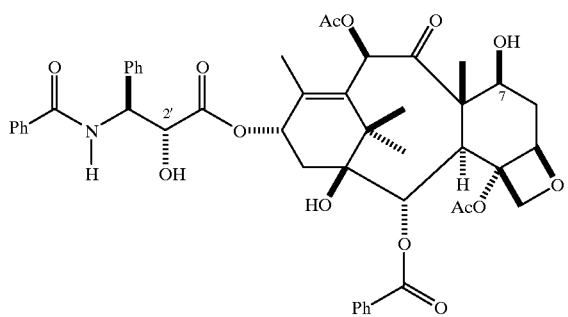

1

Although paclitaxel has demonstrated to be an unique antitumor agent, it has several disadvantages. One of the major problems is its poor solubility in water, which makes formulation difficult in relation to the intravenous administration. Due to this poor solubility, paclitaxel is formulated, using a 1:1 mixture of cremophor EL (a polyethoxylated castor oil) and ethanol (Rowinsky, E. K. et al. *J. Natl. Cancer Inst.* 1990, 82, 1247). This mixture is diluted with 5% dextrose in water or saline prior to lengthy infusion. Unfortunately, various hypertensive reactions have been reported in patients who were treated with paclitaxel, partly due to cremophor EL, which is responsible for histamine release, causing the effects (Rowinsky, E. K. et al. Ibid.). Premedication, using antihistaminic drugs can deminish these side effects, but results in additional medication, cost and discomfort to the patient.

The solubility problems with paclitaxel could be overcome by the development of a more water soluble, chemically stable, and therefore more easily formulated analog/prodrug of paclitaxel. Prodrug strategies consist of temporary modification of the physiochemical properties of a compound through chemical derivatization. Such temporary chemical modification is usually designed to alter aqueous solubility and biodistribution while the pharmacological properties of the parent drug remain intact. Prodrugs can be designed to be converted in a predictable way, in vivo, to the active drug by either an enzymatic mechanism or by hydrolysis initiated under physiological pH conditions.

SAR studies have shown that some modifications at C7 of paclitaxel are allowed ((a) Mellado, W. et al. *Biochem. Biophys. Res. Comm.* 1984, 124, 329–336. (b) Kingston, D. G. I et al. *New Trends in Nat. Prod. Chem.* 1986, 26, 219–235. (c) Horwitz, S. B. et al. *Ann. New York Acad. Sci.* 1986, 466, 733–740. (d) Kingston, D. G. I. et al. *J. Nat. Prod.* 1990, 53, 1–12. (e) Ringel, I. et al. *J. Pharmacol. Exp. Ther.* 1987, 242, 692–698. (f) Chaudhary, A. G. et al. *J. Org. Chem.* 1993, 58, 3798–3799. (g) Chen, S. et al. *J. Org. Chem.* 1993, 58, 5028–5029).

For instance, 7-acetylpaclitaxel has shown to be as active as paclitaxel in microtubule assembly assays. SAR studies have also shown that introduction of an acetyl group at C2' resulted in the loss of the ability to promote microtubule assembly. However the cytotoxic activity of 2'-acetyl-paclitaxel is almost the same as for paclitaxel, probably due to the fact that the C2'-acetyl group is either being hydrolyzed under the conditions of the bioassay or converted intracellularly to paclitaxel or an active paclitaxel metabolite. These observations suggest that the C2'- and C7-positions of paclitaxel are suitable for (temporary) structural modifications. The C2'-position seems more suitable for reversible derivatization.

Several research groups have reported the syntheses and biological evaluations of water soluble prodrugs of paclitaxel. These analogs have a polar substituent either at the C2'- or at the C7-hydroxyl group. In most cases the polar substituents are coupled to these hydroxyl groups via an ester, carbonate or carbamate functionality. Deutsch et al. (Deutsch, H. M. et al. *J. Med. Chem.* 1989, 32, 788–792) reported that some salts of 2'-succinylpaclitaxel and 2'-glutarylpaclitaxel had improved antitumor activities compared to the corresponding free acids. The triethanolamine and N-methyl-glucamine salts showed improved aqueous solubility and were more active than the sodium salts. Zhao et al. (Zhao, Z. et al. *J. Nat. Prod.* 1991, 54, 1607–1611) introduced sulfonate groups to improve the water solubility of paclitaxel. These sulfonate-paclitaxel analogs showed improved water solubility and had about the same (in vivo) activity compared to paclitaxel. Mathew et al. (Mathew, A. E. et al. *J. Med. Chem.* 1992, 35, 145–151) reported the synthesis and evaluation of some 2'- and 7-amino acid analogs of paclitaxel. The methane sulfonic salts of both 2'- and 7-amino acid esters of paclitaxel showed increased water solubility. The 2'-analogs showed activity to an extent similar to that of paclitaxel, while the others showed reduced activity. Vyas et al. (Vyas, D. M. et al. *Bioorg. Med. Chem. Lett.* 1993, 3, 1357–1360) synthesized and evaluated 2'- and 7-phosphate paclitaxel analogs. These analogs showed improved water solubility. However in vitro as well as in vivo these derivatives were non-toxic compared to paclitaxel. Ueda et al. (Ueda, Y. et al. *Bioorog. Med. Chem. Lett.* 1993, 3, 1761–1766) synthesized 2'- and 7'-phosphonoxyphenylpropionatepaclitaxel, which both showed increased water solubility. The 2'-analog was inactive, whereas the 7-analog was as active as paclitaxel in vivo. Greenwald et al. ((a) Greenwald, R. B. et al. *J. Org. Chem.* 1995, 60, 331–336. (b) Greenwald, R. B. et al. *J. Med. Chem.* 1996, 39, 424–431) prepared some 2'- and 7-polyethyleneglycol esters of paclitaxel. These analogs were extremely water soluble. The 2'-analogs had in vitro and in vivo activities in the same extent as paclitaxel, whereas the 7-analogs showed reduced activity. Greenwald et al. claimed that by choosing the appropriate weight for the 2'-PEG moiety, a prodrug was produced that is as efficacious as paclitaxel/cremophor EL/ethanol in an in vivo model. Nicolaou et al. (Nicolaou, K. C. et al. *Nature* 1993, 364, 464–466) synthesized some 2'-(2-thio-aryl)ethylcarbonate analogs of paclitaxel as well as some 2'- and 2',7-(bis)C(O)CH$_2$XCH$_2$COOH (wherein X=O, S or SO$_2$) analogs of paclitaxel, which were all more water soluble and showed increased in vitro cytotoxic activities compared to paclitaxel. Nicolaou et al. ((a) Nicolaou, K. C. et al. *Angew. Chemie* 1994, 106, 1672–1675. (b) Paloma, L. G. et al. *Chem. Biol.* 1994, 1, 107–112) also synthesized 2'- and 7-methylpyridiniumacetate analogs of paclitaxel. Both compounds showed increased water solubility. The 2'-analog was as active as paclitaxel in in vivo models, whereas the 7-analog was far less cytotoxic. Kingston et al. (Kingston et al. US patent 1995, U.S. Pat. No. 5,411,984A) prepared some 2'- and 2',7-bis-O-aroyl analogs. These analogs showed improved water solubility. The 2'-analogs showed in vivo activities in the same extent as paclitaxel and some even better.

Chemical stability is critical to the formulation and storage of any water soluble analog/prodrug of paclitaxel, since partial degradation to the poorly soluble parent drug is likely to lead to precipitation of paclitaxel. The enzymatic stability (in rat, human plasma or in vivo) is important in relation to the degradation of the prodrugs to paclitaxel or to an active metabolite of paclitaxel.

From the water soluble paclitaxel prodrugs described so far the pharmacological properties of the used solubilizing functionalities, which are released once paclitaxel is liberated have not been studied. It might be possible that these solubilizing moieties or their metabolites have some undesired and/or unknown side effects. The prodrugs described in this patent release after hydrolysis a non-toxic acid.

OBJECT OF THE INVENTION

It is therefore an object of this invention to provide water soluble paclitaxel analogs/prodrugs, using a body innocuous solubulizing moiety, for the treatment of cancer.

A further object of this invention is to produce water soluble analogs of paclitaxel which possess (in vitro or in vivo) antitumor activity in the same extent as paclitaxel.

It is a further object of this invention to produce prodrugs of paclitaxel which are stable in aqueous solutions, but which upon hydrolysis at physiological (in vitro and/or in vivo) conditions exhibit the same or similar level of antitumor activity as paclitaxel.

SUMMARY OF THE INVENTION

The above and various other objects of the present invention are achieved by water soluble analogs/prodrugs having the following general formula:

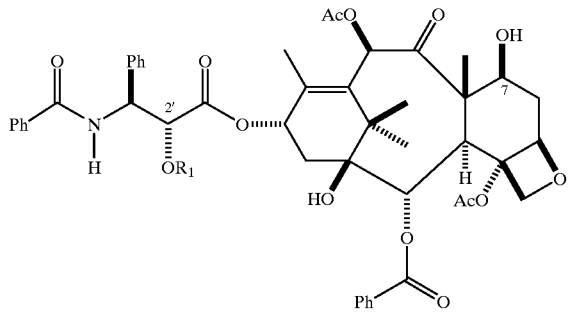

Wherein:
R$_1$=C(O)CH$_2$CH(OH)COOX
R$_2$=H, C(O)CH$_2$CH(OH)COOX,
X=H, Li, Na or any other pharmaceutically acceptable counterion.

DEFINITIONS

Unless clearly indicated by context or statement to the contrary, the terms used herein have the meanings as conventionally used in chemical arts, and definitions incorporate those used in standard texts.

DETAILED DESCRIPTION OF THE INVENTION

Paclitaxel was obtained from Pharmachemie BV Haarlem. Proton magnetic resonance spectra were measured on a Bruker AC-100 or a Bruker AM-400 spectrometer. Chemical shift values are reported as δ-values relative to tetramethylsilane as an internal standard; deuterochloroform was used as solvent. Mass spectra were obtained with a double focusing VG 7070E spectrometer. Elemental analyses were carried out on a Carlo Erba Instruments CHNSO EA 1108 element analyzer. Melting points were determined with a Reichert Thermopan microscope and are uncorrected. Thin layer chromatography was carried out on Merck precoated silica gel 60 F-254 plates (thickness; 0.25 mm). Spots were visualized with UV or a 6.2% H$_2$SO$_4$ aqueous solution, (1L) containing ammonium molybdate (42 g) and ceric ammonium sulfate (3.6 g), followed by charring. Column chromatography was carried out using silica 60 or silica 60H (Merck) Unless otherwise stated, materials were obtained from commercial sources and used without further purification. When necessary, solvents were distilled and dried according to standard procedures. All reactions, if necessary, were carried out under argon atmosphere.

The synthesis of prodrugs from paclitaxel in which the 2'-OH or the 7-OH group is esterified by a dicarboxylic acid needs a protection strategy for one of the carboxylic acid groups.

Figure 1:
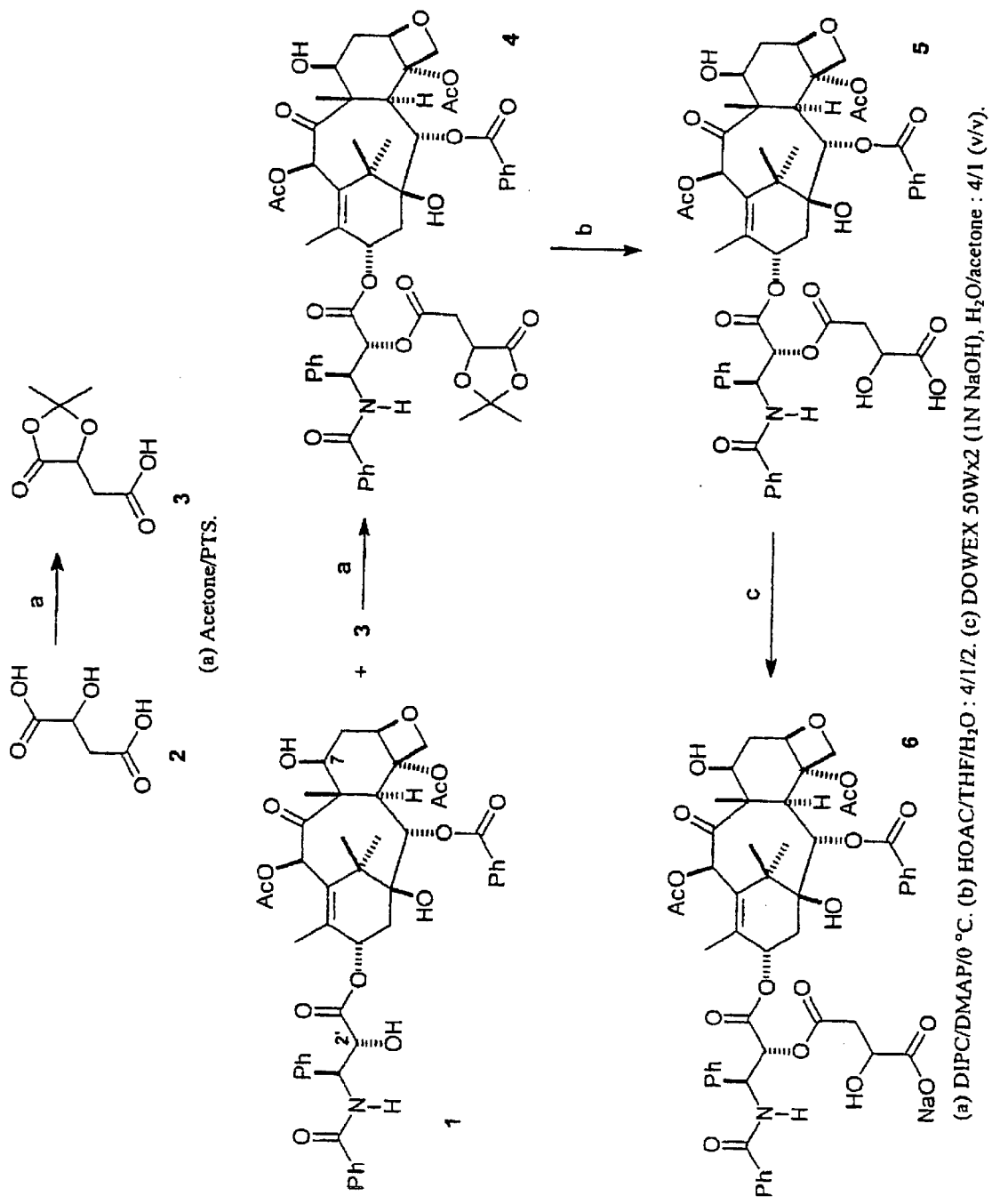
FIG. 1 illustrates the protection of one of the carboxylic acids together with the α-hydroxyl group of malic acid (2) as an isopropylidene functionality, resulting in compound 3. In this figure also the synthesis of 2'-malylpaclitaxel (5), via coupling of 3 to the C2'-hydroxyl group of paclitaxel, leading to 4, and removal of protective isopropylidine functionality, is presented. Finally it contains in conversion of 5 into the corresponding sodium salt 6.

With reference to FIG. 1, 1,2-O-(Propane-2,2-diyl)malic acid (3) was obtained after treatment with malic acid (2) with acetone, in the presence of p-toluenesulfonic acid. Next, 2'-malylpaclitaxel (5) was synthesized by reaction of paclitaxel (1) with 1.1 equivalent of 3 in the presence of diisopropylcarbodiimide (DIPC) and 4-dimethylaminopyridine (DMAP) at 0° C. to afford 2'-(1,2-O-(propane-2,2-diyl)-malyl)-paclitaxel (4), which reacted with a mixture of HOAc/THF/H$_2$O: 4/1/2 at 45° C. to give 2'-malylpaclitaxel (5). This compound 5 was subsequently eluted with a mixture of H$_2$O/acetone: 4/1 (v/v) from DOWEX 50W×2, pretreated with 1N NaOH, yielding sodium salt 6.

Figure 2:
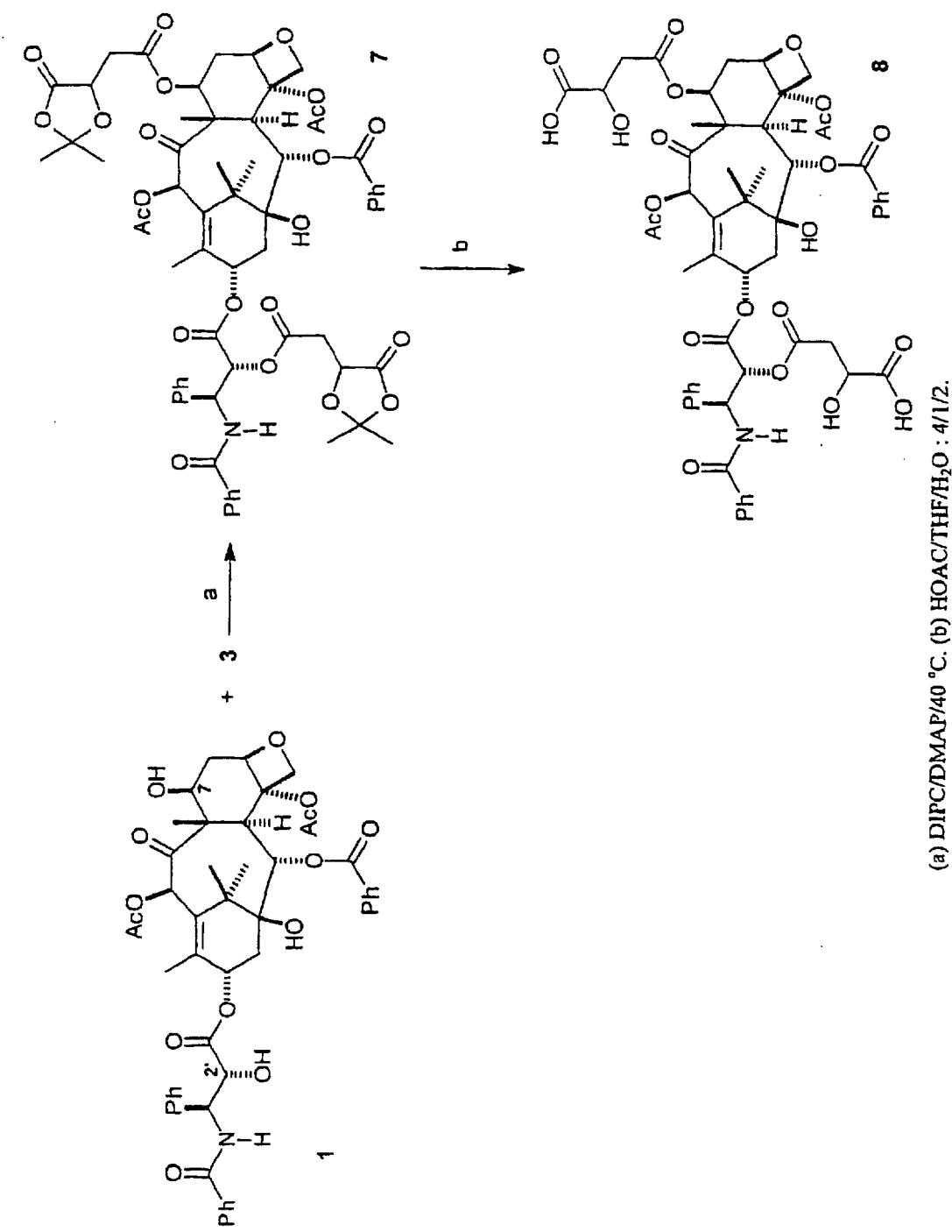
FIG. 2 illustrates the synthesis of 2',7-bis(malyl)paclitaxel (8), carried out similar to the synthesis of 5. The coupling reaction of 3 with paclitaxel, leading to 7, was carried out at 40° C.

With reference to FIG. 2, 1,2-O-(Propane-2,2-diyl)malic acid (3) was coupled to paclitaxel (1) in the presence of DIPC and DMAP at 40° C. to yield 2'7-bis(1,2-O-(propane2, 2-diyl)-malyl)-paclitaxel (7). This compound 7 was converted to 2'7-bis(malyl)paclitaxel (8) by treatment with a mixture of HOAc/THF/H$_2$O: 4/1/2. Compound 8 can be further converted into for example sodium salts analogously to the procedure described for compound 6.

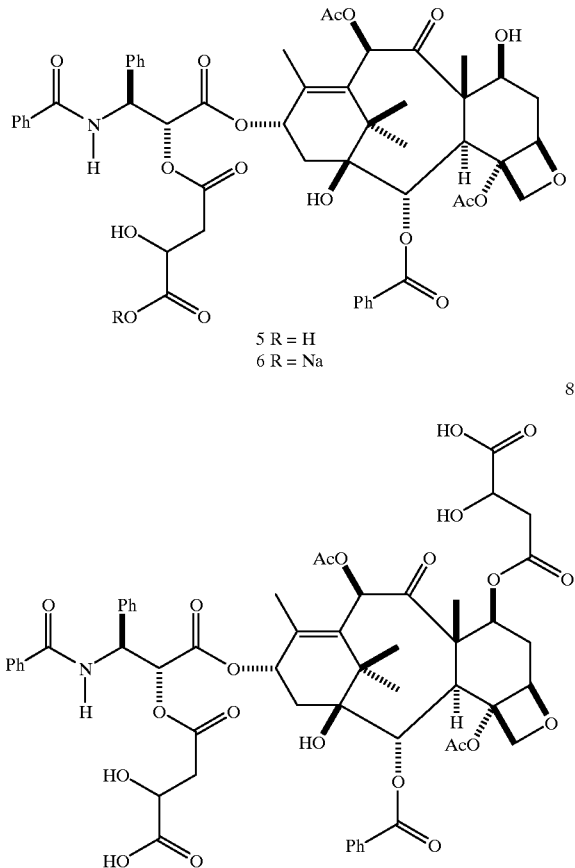

5 R = H
6 R = Na

8

Figure 3:
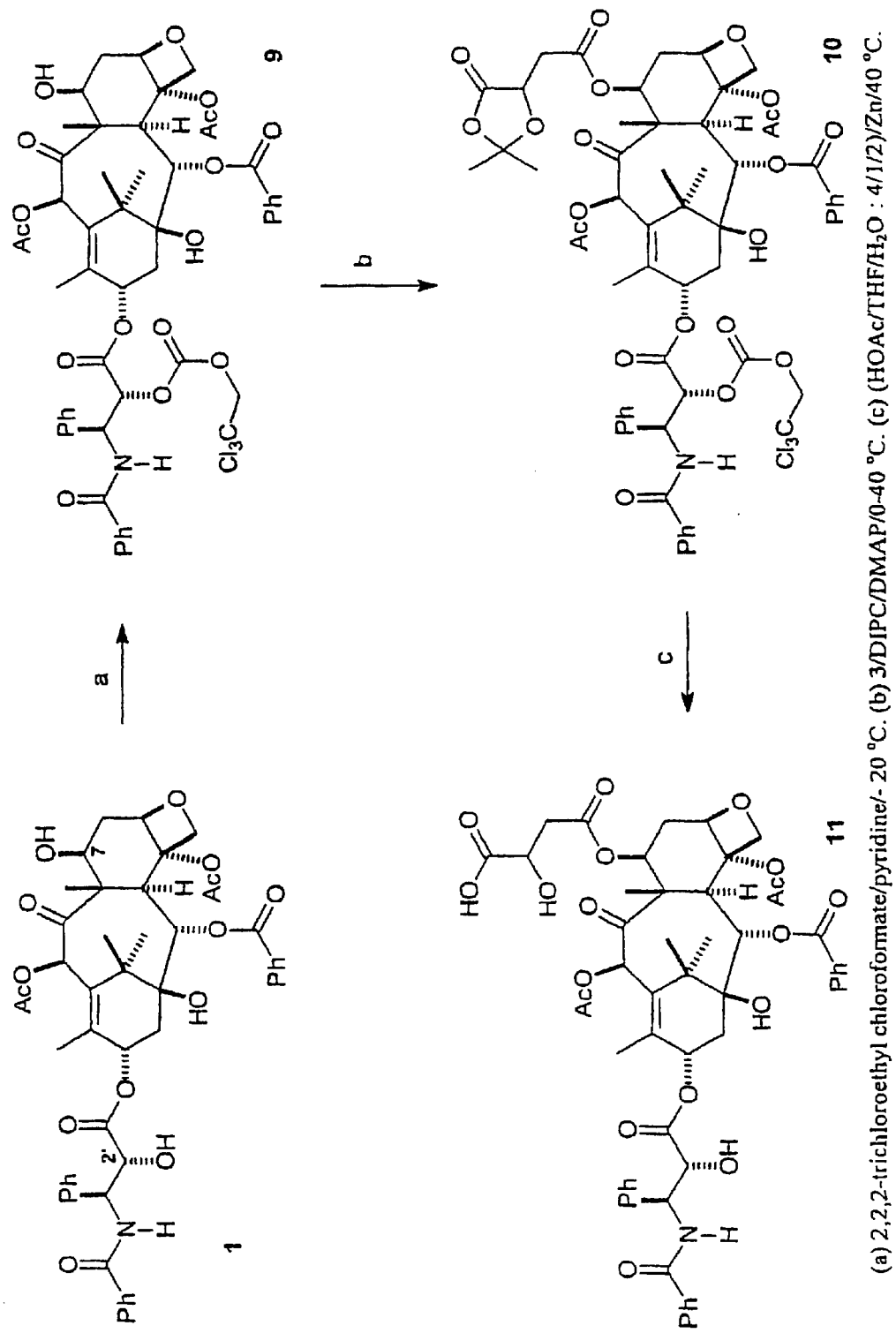
FIG. 3 illustrates the synthesis of 7-malylpaclitaxel (11), via 2'-Trocpaclitaxel (9), which was coupled to 3, leading to 10, followed by removal of the protecting groups.

With reference to FIG. 3, the C2'-hydroxyl group of paclitaxel (1) was protected, using 2,2,2-trichloroethyl chloroformate (Troc-Cl) in pyridine, leading to 2'-Trocpaclitaxel (9) (Magri, N. F. et al. *J. Org. Chem.* 1986, 51, 797–802). Compound 9 was coupled to 1,2-O-(Propane-2,2-diyl)-malic acid (3), in the presence of DIPC and DMAP to give 2'-Troc-7-(1,2-O-(propane-2,2-diyl)-malyl)paclitaxel (10). This compound 10 was converted to 7-malylpaclitaxel (11) by treatment with a mixture of HOAc/THF/H$_2$O: 4/1/2, in the presence of zinc powder (Zn).

EXAMPLES

The following nonlimiting examples provide specific synthesis methods for preparing prodrugs/analogs of paclitaxel of the present invention. All technical and scientific terms used herein have the same meaning as commonly understood by persons of ordinary skill in the art. Other methods and materials similar or equivalent to those described herein can be used in the practice or testing of the present invention.
2'-Malylpaclitaxel (5).
a. 1,2-O-(Propane-2,2-diyl)-malic acid (3).

To a solution of malic acid (2) (5.0 g, 37 mmol) and acetone (22 g, 0.37 mol) in pentane (300 ml), PTS (1.0 g, 5.8 mmol) and H$_2$SO$_4$ (10 drops) were added. The reaction mixture was heated to reflux temperature and then stirred for 18 hours. The formed water is removed azeotropically and trapped by molecular sieves (4 Å), using a Dean-Stark apparatus. After 18 hours, the reaction mixture was concentrated in vacuo. The residue was purified via chromatography (CHCl$_3$/CH$_3$CN: 1/1), yielding 3 (3.78 g, 21.7 mmol, 59%). m.p. 113° C.; $^1$H-NMR (100 MHz, CDCl$_3$) : δ 4.51 (1H, m, CH-malyl), 2.68 (2H, m, CH$_2$-malyl), 1.43 (3H, s acetonide), 1.38 (3H, s, acetonide).

b. 2'-(1,2-O-(Propane-2,2-diyl)-malyl)-paclitaxel (4). A solution of paclitaxel (1) (100 mg, 0.117 mmol) and 1,2-O (Propane-2,2-diyl)-malic acid (3) (22 mg, 0.13 mmol) in CH$_2$Cl$_2$ (10 ml) was stirred at 0° C. Next, DIPC (36 μl, 0.24 mmol) and DMAP (15 mg, 0.12 mmol) were added. After stirring for 3 hours at 0° C., the mixture was diluted with EtOAc (25 ml) and washed with a saturated NaHCO$_3$ solution. The organic layer was washed with water, dried over Na$_2$SO$_4$ and concentrated in vacuo. The residue was purified via chromatography (EtOAc/hexane: 1/1), yielding 4 (103 mg, 0.102 mmol, 87%) m.p. 138° C.; $^1$H-NMR (400 MHz, CDCl$_3$): δ 8.15 (2H, d, J=7.2 Hz, H-Ph), 7.80 (2H, d, J=7.4 Hz, H-Ph), 7.61 (1H, t, J=7.2 Hz, H-Ph) , 7.45 (10H, m, H-Ph) 7.01 (1H, d, J$_{NH-3'}$=9.2 Hz, NH), 6.29 (1H, s, H10), 6.26 (1H, m, H13) , 6.00 (1H, dd, J$_{3'-NH}$=9.2 Hz, J$_{3'-2'}$=3.0 Hz, H3'), 5.69 (1H, d, J$_{2-3}$=7.1 Hz, H2), 5.52 (1H, d, J$_{2'-3'}$=3.0 Hz, H2'), 4.97 (1H, d, J$_{5-6}$=8.0, H5), 4.44 (1H, m, H7), 4.32 (1H, d, J$_{20a-20b}$=8.4 Hz, H20a), 4.21 (1H, d, J$_{20b-20a}$=8.4 Hz, H20b), 4.12 (1H, m, CH-malyl), 3.82 (1H, d, J$_{3-2}$=7.1 Hz, H3), 2.96 (2H, m, CH$_2$-malyl), 2.51 (1H, m, H6), 2.46 (3H, s, OCOCH$_3$), 2.36 (1H, m, H14a), 2.23 (3H, s, OCOCH$_3$), 2.19 (1H, m, H14b), 2.03 (1H, m, H6), 1.93 (1H, s, H18), 1.69 (3H, s, H16), 1.57 (3H, s, acetonide), 1.51 (3H, s, acetonide), 1.25 (3H, s, H17), 1.13 (3H, s, H19); FAB-MS, 1010 [M+H]$^+$, 1032 [M+Na]$^+$.

c. 2'-Malylpaclitaxel (5). Compound 4 (100 mg, 0.099 mmol) was dissolved in a mixture of HOAc/THF/H$_2$O (8/2/4 ml). The mixture was stirred at 45° C. for 6 hours. Next, the organic solvents were removed by evaporation in vacuo. The residue was diluted by water (100 ml) and freeze dried, yielding 5 (91 mg, 0.093 mmol, 94%). m.p. 148–151° C. $^1$H-NMR (400 MHz, CDCl$_3$) : δ 8.16 (2H, d, J=7.6 Hz, H-Ph), 7.93 (2H, d, J=7.6 Hz, H-Ph), 7.61 (1H, t, J=7.3 Hz, H-Ph), 7.36 (11H, m, H-Ph and NH), 6.30 (1H, s, H10), 6.28 (1H, m, H13), 6.08 (1H, dd, J$_{3'-NH}$32 9.2 Hz, J$_{3'-2'}$=2.8 Hz, H3'), 5.68 (1H, d, J$_{2-3}$=7.3 H d, J$_{5-6}$=8.0, H5), 4.46 (1H, m, H7), 4.33 (1H, d, J$_{20a-20b}$=8.4 Hz, H20a), 4.27 (1H, m, CH-Malyl), 4.22 (1H, d, J$_{20b-20a}$=8.4 Hz, H20b), 3.82 (1H, d, J$_{3-2}$=7.3 Hz, H3), 3.03 (2H, m, CH$_2$-malyl), 2.55 (1H, m, H6), 2.53 (3H, s, OCOCH$_3$), 2.40 (1H, m, H14a), 2.23 (3H, s, OCOCH$_3$), 2.13 (1H, m, H14b), 1.93 (1H, s, H18), 1.88 (1H, m, H6), 1.69 (3H, s, H16), 1.21 (3H, s, H17), 1.14 (3H, s, H19); FAB-MS, 992 [M+Na]$^{30}$ .
Sodium salt of 2'-malylpaclitaxel (6).

2'-Malylpaclitaxel (5) (30 mg, 0.031 mmol) was brought on DOWEX 50W×2, which was pretreated with 1N NaOH (aq). Using a mixture of H$_2$O and acetone (4/1, v/v) as eluent, sodium salt 6 (30 mg, 0.030 mmol, 98%) was isolated after removal of the acetone in vacuo and freeze drying. m.p. 195° C.; $^1$H-NMR (400 MHz, CDCl$_3$): in accordance with the structure of compound 5; FAB-MS, 992 [M+H]$^+$, 1014 [M+Na]$^+$.
2', 7-Bis(malyl)paclitaxel (8).

a. 2', 7-Bis(1,2-O-(propane-2,2-diyl)-malyl)-paclitaxel (7). A solution of paclitaxel (1) (50 mg, 0.0586 mmol) and 1,2-O(Propane-2,2-diyl)-malic acid (3) (51 mg, 0.29 mmol) in CH$_2$Cl$_2$ (5 ml) was stirred at 0° C. Next, DIPC (100 μl, 0.064 mmol) and DMAP (7.5 mg, 0.061 mmol) were added. After 1 hour, the mixture was heated to reflux temperature and stirred for 3 days. The mixture was filtered over Hyflo. The filtrate was diluted with CH$_2$Cl$_2$ (30 ml) and washed with a saturated NaHCO$_3$ solution. The organic layer was washed with water, dried over Na$_2$SO$_4$ and concentrated in vacuo. The residue was purified via chromatography (EtOAc/hexane 1/1), yielding 7 (49 mg, 0.0421 mmol, 72%). m.p. 139° C.; $^1$H-NMR (400 MHz, CDCl$_3$): δ 8.14 (2H, d, J=7.6 Hz, H-Ph), 7.80 (2H, d, J=7.6 Hz, H-Ph), 7.61 (1H, t, J=7.4 Hz, H-Ph), 7,39 (10H, m, H-Ph), 7.02 (1H, d, $J_{NH-3'}$=9.2 Hz, NH), 6.24 (1H, s, H10), 6.23 (1H, m, H13), 5.99 (1H, dd, $J_{3'-NH}$=9.2 Hz, $J_{3'-2'}$=3.0 Hz, H3'), 5.69 (1H, d, $J_{2-3}$=6.9 Hz, H2), 5.66 (1H, m, H7), 5.55 (1H, d, $J_{2'-3'}$=3.0 Hz, H2), 4.97 (1H, d, $J_{5-6}$=9.4, H5), 4.84 (1H, m, CH-malyl), 4.64 (1H, m, CH-malyl), 4.33 (1H, d, $J_{20a-20b}$=8.4 Hz, H20a), 4.19 (1H, d, $J_{20b-20a}$=8.4 Hz, H20b), 3.94 (1H, d, $J_{3-2}$=6.9 Hz, H3), 3.10 (2H, m, CH$_2$-malyl), 2.97 (2H, m, CH$_2$-malyl), 2.60 (1H, m, H6), 2.45 (3H, s, OCOCH$_3$), 2.35 (1H, m, H14a), 2.25 (1H, m, H14b), 2.21 (3H, s, OCOCH$_3$), 1.97 (1H, s, H18), 1.85 (1H, m, H6), 1.81 (3H, s, H16), 1.58 (6H, s, acetonide), 1.56 (6H, s, acetonide), 1.21 (3H, s, H17), 1.16 (3H, s, H19); FAB-MS, 1166 [M+H]$^+$.

b. 2'7-Bis(malyl)paclitaxel (8). Compound 7 (40 mg, 0.0343 mmol) was dissolved in a mixture of HOAc/THF/H$_2$O (4/1/2 ml). The mixture was stirred at 45° C. for 6 hours. Next, the organic solvents were removed by evaporation in vacuo. The residue was diluted by water (50 ml) and freeze dried, yielding 8 (33 mg, 0.0304 mmol, 89%). m.p. 166–168° C.; $^1$H-NMR (400 MHz, CDCl$_3$): δ 8.11 (2H, d, J=7.6 Hz, H-Ph), 7.84 (2H, d, J=7.5 Hz, H-Ph), 7.63 (1H, t, J=7.5 Hz, H-Ph), 7.37 (11H, m, H-Ph and NH), 6.25 (1H, s, H10), 6.16 (1H, m, H13), 5.99 (1H, dd, $J_{3'-NH}$=8.8 Hz, $J_{3'-2'}$=2.9 Hz, H3'), 5.67 (1H, d, $J_{2-3}$=6.4 Hz, H2), 5.66 (1H, m, H7), 5.63 (1H, d, $J_{2'-3'}$=2.8 Hz, H2'), 4.94 (1H, d, $J_{5-6}$=7.6, H5), 4.48 (2H, m, CH-malyl), 4.32 (1H, d, $J_{20a-20b}$=7.9 Hz, H20a), 4.17 (1H, d, $J_{20b-20a}$=7.9 Hz, H20b), 3.88 (1H, d, $J_{3-2}$=6.4 Hz, H3), 2.97 (4H, m, CH$_2$-malyl), 2.51 (1H, m, H6), 2.44 (3H, s, OCOCH$_3$), 2.36 (2H, m, H14), 2.07 (3H, s, OCOCH$_3$), 1.93 (1H, s, H18), 1.86 (1H, m, H6), 1.79 (3H, s, H16), 1.20 (3H, s, H17), 1.18 (3H, s, H19); FAB-MS, 1108 [M+Na]$^+$.

7-Malylpaclitaxel (11).

a. 2'-Trocpaclitaxel (9). A solution of paclitaxel (1) (80 mg, 0.0938 mmol) in CH$_2$Cl$_2$ (2 ml) and pyridine (0.2 ml) was stirred at −23° C. Next, 2,2,2-trichloroethyl chloroformate (13 μl, 0.095 mmol) was added. After stirring for one hour at −23° C., the mixture was diluted with CH$_2$Cl$_2$ (20 ml) and washed with 1N HCl (aq). The organic layer was washed with a saturated NaHCO$_3$ solution, with water, dried over Na$_2$SO$_4$ and concentrated in vacuo. The residue was purified via chromatography (EtOAc/hexane: 1/1), yielding 9 (63 mg, 0.0612 mmol, 65%). m.p. 171° C. (dec); $^1$H-NMR (400 MHz, CDCl$_3$): δ 8.15 (2H, d, J=7.4 Hz, H-Ph), 7.75 (2H, d, J=7.5 Hz, H-Ph), 7.61 (1H, t, J=7.4 Hz, H-Ph), 7.44 (10 H, m, H-Ph), 6.93 (1H, d, $J_{NH-3'}$=9.4 Hz, NH), 6.29 (1H, s, H10), 6.25 (1H, t, $J_{13-14}$=8.8 Hz, H13), 6.05 (1H, dd, $J_{3'-NH}$=9.3 Hz, $J_{3'-2'}$=2.8 Hz, H3'), 5.69 (1H, d, $J_{2-3}$=7.3 Hz, H2), 5.54 (1H, d, $J_{2'-3'}$=2.7 Hz, H2'), 4.97 (1H, dd, J=9.4 Hz, J=1.6 Hz, H5), 4.78 (2H, d, J=8.0 Hz, CH$_2$ (Troc)), 4.43 (1H, m, H7), 4.32 (1H, d, $J_{20a-20b}$=8.4 Hz, H20a), 4.21 (1H, d, $J_{20b-20a}$=8.4 Hz, H20b), 3.82 (1H, d, $J_{3-2}$=7.2 Hz, H3), 2.55 (1H, m, H6), 2.48 (3H, s, OCOCH$_3$), 2.40 (1H, m, H14a), 2.23 (3H, s, OCOCH$_3$), 2.20 (1H, m, H14b), 1.91 (3H, s, H18), 1.88 (1H, m, H6), 1.69 (3H, s, H16), 1.24 (3H, s, H17), 1.14 (3H, s, H19); FAB-MS, 1030 [M+H]$^+$, 1052 [M+Na]$^+$.

b. 2'-Troc-7-(1,2-O-(propane-2,2-diyl)-malyl)paclitaxel (10).

A solution of 9 (63 mg, 0.0612 mmol) and 3 (21 mg, 0.12 mmol) in CH$_2$Cl$_2$ (5 ml) was stirred at 0° C. Next, DIPC (125 μl, 0.80 mmol) and DMAP (20 mg, 0.16 mmol) were added. After 1 hour, the mixture was heated to reflux temperature and then stirred for 3 days. The mixture was filtered over Hyflo. The filtrate was diluted with CH$_2$Cl$_2$ (50 ml) and washed with a saturated NaHCO$_3$ solution. The organic layer was washed with water, dried over Na$_2$SO$_4$ and concentrated in vacuo. The residue was purified via chromatography (EtOAc/hexane: 2/5), yielding 10 (38 mg, 0.0320, 52%). m.p. 140–145° C.; $^1$H-NMR (400 MHz, CDCl$_3$): δ 8.14 (2H, d, J=7.3 Hz, H-Ph), 7.76 (2H, d, J=7.5 Hz, H-Ph), 7.61 (1H, t, J=7.5 Hz, H-Ph), 7.45 (10H, m, H-Ph), 6.92 (1H, d, $J_{NH-3'}$=9.5 Hz, NH), 6.26 (1H, s, H10), 6.25 (1H, m, H13, 6.04 (1H, dd, $J_{3'-NH}$=9.6 Hz, $J_{3'-2'}$=2.8 Hz, H3'), 5.69 (1H, d, $J_{2-3}$=6.8 Hz, H2), 5.65 (1H, m, H7), 5.54 (1H, d, $J_{2'-3'}$=2.8 Hz, H2'), 4.99 (1H, d, $J_{5-6}$=8.4, H5), 4.84 (1H, m, CH-malyl), 4.78 (2H, d, J=9.4 Hz, CH$_2$ (Troc)), 4.33 (1H, d, $J_{20a-20b}$=8.4 Hz, H20a), 4.20 (1H, d, $J_{20b-20a}$=8.4 Hz, H20b), 3.95 (1H, d, $J_{3-2}$=6.8 Hz, H3), 3.07 (2H, m, CH$_2$-malyl), 2.63 (1H, m, H6), 2.47 (3H, s, OCOCH$_3$), 2.40 (1H, m, H14a), 2.25 (1H, m, H14b), 2.16 (3H, s, OCOCH$_3$), 1.97 (1H, s, H18), 1.87 (1H, m, H6), 1.81 (3H, s, H16), 1.60 (3H, s, acetonide), 1.57 (3H, s, acetonide), 1.24 (3H, s, H17), 1.14 (3H, s, H19); FAB-MS, 1187 [M+Na]$^+$, 1209 [M+Na]$^+$.

c. 7-Malylpaclitaxel (11). Compound 10 (28 mg, 0.0236 mmol) was dissolved in a mixture of HOAc/THF/H$_2$O (4/1/2 ml). Zinc powder (20 mg) was added. The mixture was stirred for 3 hours at 45° C. Next, the organic solvents are evaporated in vacuo. The residue was diluted with water (50 ml) and freeze dried, yielding 11 (23 mg, 0.0237 mmol, 100%). m.p. 237–240° C.; $^1$H-NMR (400 MHz, CDCl$_3$): δ 8.13 (2H, d, J=7.3 Hz, H-Ph), 7.76 (2H, d, J=7.3 Hz, H-Ph), 7.61 (1H, t, J=7.4 Hz, H-Ph), 7.38 (10H, m, H-Ph), 6.93 (1H, d, $J_{NH-3}$=9.2 Hz, NH), 6.25 (2H, m, H10 and H13), 5.75 (1H, dd, $J_{3'-NH}$=9.2 Hz, $J_{3'-2'}$=2.8 Hz, H3'), 5.69 (1H, d, $J_{2-3}$=7.1 Hz, H2), 5.66 (1H, m, H7), 4.96 (1H, d, $J_{5-6}$=8.4, H5), 4.83 (1H, d, $J_{2'-3'}$=2.8 Hz, H2'), 4.74 (1H, m, CH-malyl), 4.28 (1H, d, $J_{20a-20b}$=8.0 Hz, H20a), 4.14 (1H, d, $J_{20b-20a}$=8.0 Hz, H20b), 3.95 (1H, d, $J_{3-2}$=7.1 Hz, H3), 3.06 (2H, m, CH$_2$-malyl), 2.60 (1H, m, H6), 2.47 (3H, s, OCOCH$_3$), 2.38 (1H, m, H14a), 2.25 (1H, m, H14b), 2.16 (3H, s, OCOCH$_3$), 1.97 (1H, s, H18), 1.81 (3H, s, H16), 1.25 (3H, s, H17), 1.14 (3H, s, H19); FAB-MS, 970 [M+H]$^+$, 992 [M+Na]$^+$.

Solubility and Stability

Methods:

Water Solubility: Paclitaxel or paclitaxel prodrugs (5, 6, 8, 11) were suspended in water or PBS-buffer (pH 7.4) until a concentration was reached of 2 mg/ml. The suspensions were sonicated for 15 minutes and centrifuged (13000 g) for 10 minutes (Nicolaou, K. C. et al. *Nature* 1993, 364, 464–466). The above fluid was analyzed, using HPLC. The paclitaxel (prodrug) concentration was determined using paclitaxel standards in methanol.

HPLC: Rheodyne injection valve (20 μl loop); Lichrospher 5RP18 column (200×3 mm, Chrompack); UV-detector (Model 759A, Applied Biosystems); eluent: CH$_3$CN/ MeOH/H$_2$O: 5/1/4 in 10 mM NH$_4$OAc (pH 5.0) (Willey, T. A. *J. Chromatography* 1993, 621, 231–238). The detection of the (pro)drugs was performed at 226 nm, where it is supposed that the extinction coefficients of paclitaxel and paclitaxel prodrugs are equal. The concentrations were determined by measuring the relative area of paclitaxel or the paclitaxel prodrugs.

Stability in Human Plasma and PBS-buffer:

The paclitaxel prodrugs (5, 6, 8, 11) were dissolved in water, sonicated and centrifuged. 100 μl of the above fluid was mixed with 400 μl of plasma (heparin) or PBS-buffer (pH7.4), respectively, in such way that the concentration of the prodrug was about 0.5 mg/mL. The plasma or PBS-buffer, respectively, was incubated at 37° C. and on different points in time (T=0, 0.5, 1, 4, 20, 48 hours) 50 μl was extracted with 150 μl of EtOAc. After mixing for 2 minutes (using a vortex), this mixture was centrifuged (2 minutes, 13000 g) and 100 μl EtOAc was evaporated (30 minutes, in vacuo). The (pro)drugs were dissolved in 50 μl eluent and analyzed by HPLC (Longnecker, S. M. *Cancer Treat Rep.* 1987, 71, 53–59). The efficiency for the extraction of paclitaxel was about 80%.

Solubility and stability values for compounds of the present invention are shown in table I.

plates (Costar, no. 3799, Badhoevedorp, The Netherlands). The plates were preincubated 24 hr at 37° C., 5% $CO_2$ to allow the cells to adhere.

On day 2, 100 µl of the highest drug concentration was added to the wells of column 12 and from there diluted

TABLE I

Solubility and Stability of some Water-soluble Analogs of Paclitaxel

| No | 2'-(R$_1$)paclitaxel<br>R$_1$ = | 7-(R$_2$)paclitaxel<br>R$_2$ = | Water<br>Solubility<br>(mg/ml) | $T_{1/2}{}^a$ (hours) | |
|---|---|---|---|---|---|
| | | | | pH 7.4 | Human Plasma |
| 1 | H | H | 0.01 | — | — |
| 5 | C(O)CH$_2$CH(OH)COOH | H | 0.2 | >24 | 20 |
| 6 | C(O)CH$_2$CH(OH)COONa | H | 0.6 | no pacl.$^b$ | 4 |
| 8 | C(O)CH$_2$CH(OH)COOH | C(O)CH$_2$CH(OH)COOH | 0.5 | no pacl.$^b$ | no pacl.$^b$ |
| 11 | H | C(O)CH$_2$CH(OH)COOH | 0.003 | no pacl.$^b$ | no pacl.$^b$ |

$^a$The stability of an analogs is given as half-live values ($T_{1/2}$), the time in which 50% of the analog is degraded to paclitaxel.
$^b$No liberated paclitaxel was detected.

With the exception of 11, all prodrugs showed increased water solubility compared with paclitaxel. Best water solubility was found for the 2'-malyl prodrug 6. All malyl prodrugs 5, 6, 8 and 11, showed sufficient stability in PBS buffer for prodrug applications. Prodrug 6 showed also a fast hydrolysis rate in human plasma. These results show that the most promising drug for further evaluation of the drugs presented in table I is the malyl prodrug 6.

Biological Evaluation

Material and Methods:

Determination of the $IC_{50}$-values for the new synthesized prodrugs have been determined with a variety of cell lines and have been compared with the $IC_{50}$-value of paclitaxel 1 (see table II) Compounds 1, 5, 8, 11,:

The following human tumor cell lines were used:

MCF7 Breast cancer

EVSA-T Breast cancer

WIDR Colon cancer

IGROV Ovarian cancer

M19 MEL Melanoma

A498 Renal cancer

HA266 non small cell lung cancer

MCF7 is estrogen receptor ER+/Progesterone receptor PgR+ and EVSA-T is ER-/PgR-.

Cell lines WIDR, M19 MEL, A498 and IGROV belong to the currently used anti-cancer screening panel of the National Cancer Institute, USA (Skeham et al., *J. Nat. Cancer Inst.* 85: 1107–1112, 1990).

Prior to the experiments a myocoplasma test was carried out on all cell lines and found to be negative. All cell lines, except ETSA-T, were maintained in a continuous logarithmic culture in RPMI medium with Hepes and Phenol red supplemented with 10% bovine calf serum (BCS), penicillin 111 IU/ml, streptomycin 111 µg/ml, gentamycin 46 µg/ml and insulin 10.6 µg/ml. EVSA-T was maintained in DMEM with 5% BCS and antibiotics as described. The cells were mildly trypsinized for passage and for use in experiments.

The Experiment:

The compounds of this invention were dissolved to a concentration of 177147 ng/ml as follows:

Paclitaxel 5% DMSO in full RPMI growth medium 5 5% DMSO in full RPMI growth medium 8 5% DMSO in full RPMI growth medium 11 5% DMSO in full RPMI growth medium On day 0, 200 µl of trypsinized tumor cells (2*10$^3$ cells/well) were plated in 96-wells flatbottom microtiter 3-fold to column 3 by serial transfer of 100 µl using an 8 channel micropipette. The final volume of column 3 was adjusted to 200 µl with PBS. Column 2 was used for the blank. To column 1 PBS was added to diminish interfering evaporation.

On day 7 the incubation was terminated by washing the plates twice with PBS. Subsequently the cells were fixed with 10% trichloroacetic acid in Milli Q water (Millipore, Etten Leur, The Netherlands) and placed at 4° C. for one hour.

After five washings with tap water, the cells were stained for at least 15 min. with 0.4% SRB, dissolved in 1% acetic acid, and subsequently washed with 1% acetic acid to remove the unbound stain. The plates were air dried and the bound protein was dissolved by using 150 µl 10 mmol/l tris base. The absorbance was read at 540 nm using an automatic microplate reader (Titertec, Flow Laboratories LtD., Irvine, Scotland). Data were used for construction of concentration-response curves and determination of the $IC_{50}$-value.

Compounds 1, 6:

The human tumor cell line OVCAR-3 was used. OVCAR is an ovarium carcinoma.

In vitro antiproliferative effects: paclitaxel or paclitaxel prodrugs were dissolved in DMSO to give a concentration of 5 mM. Concentrations were verified by measuring the OD at 226 nm. The antiproliferative effects of drugs and prodrugs were determined with the use of OVCAR-3 cells. Cells in supplemented tissue culture medium (DMEM, 10% fetal calf serum with 50 IU/ml penicillin and 50 microgram/ml streptomycin) were seeded in triplicate in 96-well culture plates (5000/well, 100 microliter). After 24 h, 100 microliter of culture medium containing drug or prodrug was added to give final concentrations ranging from 1 picomolar to 10 micromolar.

The cells were incubated for an additional 72 h, fixed with 10% trichoroacetic acid and stained with sulforhodamine B. The absorbance at 540 nm was read and the antiproliferative effects were expressed as $IC_{50}$ values, inhibition when compared with control cell growth (Houba et al. *Bioconj. Chem.* 1996, 7, 606–611).

The $IC_{50}$ values of the compounds of this invention are given in table II.

TABLE II

| | $IC_{50}^a$ (ng/ml) | | | | | | | $IC_{50}^a$ (nM) |
|---|---|---|---|---|---|---|---|---|
| Compound | MCF7 | EVSA-T | WIDR | IGROV | M19 MEL | A498 | H226 | OVCAR-3 |
| paclitaxel | <3 | <3 | <3 | 33 | <3 | 5 | <3 | 0.25 |
| 5 | <3 | <3 | <3 | <3 | 3 | 39 | 10 | — |
| 6 | <3 | <3 | <3 | 233 | <3 | <3 | <3 | 0.80 |
| 8 | 69 | 59 | 167 | 49 | 311 | 436 | 241 | — |
| 11 | 390 | 300 | 589 | 241 | 1344 | 1435 | 706 | — |

$^a IC_{50}$: Drug concentration required to inhibit cell proliferation to 50% vs untreated cells (37° C. 72 h)

Evaluation and Conclusions

With exception of compound 11, all the analogs of paclitaxel show increased water solubility relative to paclitaxel.

Compounds 8 and 11 showed reduced cytotoxic activity, when compared to paclitaxel, probably due to the functional group at C7-OH. The 7-analog (11) and the 2',7-analog (8) is very stable: in PBS-buffer (pH 7.4) as well as in human plasma, no degradation to the parent drug was observed, since no liberated paclitaxel has been detected.

Compound 5 showed similar cytotoxic activity as paclitaxel, which can probably be explained by the degradation of these compounds to the parent drug, under the conditions used to determine the activity. The 2'-analog 5 is stable in PBS-buffer (pH 7.4). After 24 hours, only traces of paclitaxel were detected. Whereas in human plasma only after 20 hours 50% of the analog is degraded to paclitaxel.

Compound 6 showed a comparable against OVCAR-3 cells, when compared to paclitaxel. Of compound 6 about 500 was degraded to paclitaxel within 4 hours. Furthermore, compound 6 is sixty times more watersoluble than paclitaxel.

The present invention discloses a method for the preparation of paclitaxel analogs of paclitaxel having a malate moiety at C2' and/or C7-position. It is apparent that many modifications of the present invention are possible, for example the use of counterions other than sodium, which may give rise to higher solubilities. It is therefore understood that the invention may be practiced otherwise than specifically described.

We claim:

1. Water soluble antitumor analogs of paclitaxel having the following formula:

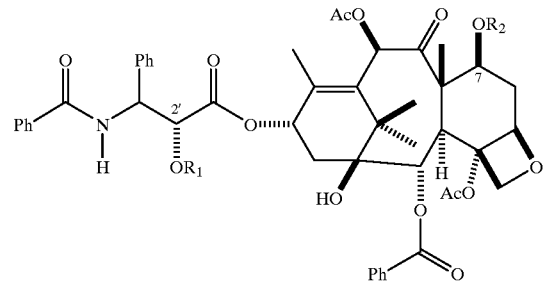

wherein:
$R_1$=C(O)CH$_2$CH(OH)COOX,
$R_2$=H, C(O)CH$_2$CH(OH)COOX,
X=H, Li, Na or any other pharmaceutically acceptable counterion.

2. A pharmaceutical composition comprising an antineoplastically effective amount of the analog of claim 1 as an active ingredient, and pharmaceutically acceptable carrier, optionally in combination with further additives.

3. A method for the treatment of tumours comprising administering an effective amount of the analog as defined in claim 1.

4. A method in accordance with claim 3, wherein said tumour is a mammary carcinoma or a colon tumour.

* * * * *